US006486346B1

(12) United States Patent
Heitkämper et al.

(10) Patent No.: US 6,486,346 B1
(45) Date of Patent: Nov. 26, 2002

(54) PROCESS FOR THE PREPARATION OF DURENE DIISOCYANATE

(75) Inventors: Peter Heitkämper, Dormagen (DE); Klaus Jost, Dormagen (DE); Stefan Penninger, Pulheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/460,953

(22) Filed: Dec. 14, 1999

(30) Foreign Application Priority Data

Dec. 22, 1998 (DE) .......................... 198 59 297

(51) Int. Cl.[7] ..................... C07C 273/00; C07C 263/00; C07C 205/00
(52) U.S. Cl. ................... 560/335; 560/342; 568/932
(58) Field of Search ................... 560/335, 342; 568/932

(56) References Cited

U.S. PATENT DOCUMENTS

| 2,864,871 | A | * | 12/1958 | Moringstar | ................ | 568/932 |
| 3,089,862 | A | | 5/1963 | Fetterly et al. | ............... | 260/75 |
| 3,153,099 | A | | 10/1964 | Lind et al. | .................. | 260/645 |
| 3,824,266 | A | * | 7/1974 | Dietrich et al. | ............. | 560/335 |
| 3,828,089 | A | * | 8/1974 | Hammond et al. | ......... | 560/342 |
| 4,207,212 | A | * | 6/1980 | Nefedov et al. | ............ | 502/252 |
| 4,618,706 | A | * | 10/1986 | Scholl et al. | ............... | 560/335 |
| 5,367,108 | A | * | 11/1994 | Blank et al. | ................ | 568/932 |

FOREIGN PATENT DOCUMENTS

DE 33 17 649 11/1984

OTHER PUBLICATIONS

Journal of the American Chem. Soc., vol. 70, May–Sep. 1948, Editor Arthur B. Lamb, p. 2227, The Autoxidation of the p–Phenylenediamines.
Journal of the American Chem. Soc., vol. 72, Jan.–Apr. 1950, pp. 132–135, Adams et al, Restricted Rotation in Aryl Almines. IX. Diaminodurene Derivatives.

* cited by examiner

Primary Examiner—Alan L. Rotman
Assistant Examiner—Taylor V. Oh
(74) Attorney, Agent, or Firm—Joseph C. Gil; Lyndanne M. Whalen; Carolyn M. Sloane

(57) ABSTRACT

Durene diisocyanate is prepared by reacting durene with nitric acid in sulfuric acid, catalytic hydrogenation of the dinitrodurene that is formed, and phosgenation of the resultant durene diamine in a conventional manner. The intermediate products dinitrodurene and durene diamine do not have to be worked up in a complicated manner as solid products, but can be worked up in dissolved form. The intermediate products dinitrodurene and durene diamine do not have to be isolated and purified in a complicated manner. but can be processed directly after preparation. Another advantage of this process is that only a single organic solvent need be used for the overall preparation process. Separation and re-use of spent acid in the conversion of durene with nitric acid also renders the process of the present invention significantly less environmentally harmful than the known processes of the prior art.

13 Claims, No Drawings

PROCESS FOR THE PREPARATION OF DURENE DIISOCYANATE

BACKGROUND OF THE INVENTION

The present invention relates to an improved process for the preparation of 2,3,5,6-tetramethyl-1,4-diisocyanatobenzene (hereinafter referred to as "durene diisocyanate") by (1) reaction of 1,2,4,5-tetramethylbenzene (hereinafter referred to as "durene") with nitric acid in sulfuric acid, (2) catalytic hydrogenation of the resultant 2,3,5,6-tetramethyl-1,4-dinitrobenzene (hereinafter referred to as "dinitrodurene"), and (3) phosgenation of the resultant 2,3,5,6-tetramethyl-1,4-diaminobenzene (hereinafter referred to as "durene diamine").

The preparation of durene diisocyanate is known. One of the known processes is described in British Patent Specification 779,806. In accordance with British Patent 779,806, durene diamine is dissolved in chlorobenzene, then reacted with gaseous hydrogen chloride to form durene diamine dihydrochloride, and the latter is further reacted as a suspension in chlorobenzene with phosgene at elevated temperature.

Durene diamine has been known for a long time and is normally prepared from dinitrodurene by reduction. The hydrogenation of dinitrodurene to durene diamine in ethanol with the addition of Raney nickel as catalyst is described, for example, in the *Journal of the American Chemical Society*, Vol. 70, p. 2227 and Vol. 72, p. 132.

Dinitrodurene has similarly been known for a long time and is normally prepared by nitration of durene. An improved process for the preparation of dinitrodurene is described in U.S. Pat. No. 3,153,099. In accordance with U.S. Pat. No. 3,153,099, a suspension of durene inconcentrated aqueous sulfuric acid is reacted with a nitric acid-sulfuric acid-water mixture in the absence of organic solvents at temperatures from 5° to 10° C., the resultant suspension is then stirred into an ice-water mixture and the dinitrodurene is filtered off, washed with water, and dried at 60° to 70° C.

U.S. Pat. No. 3,153,099 teaches, the obvious procedure of dissolving durene in an organic solvent and subjecting this solution to a nitration has a considerable number of disadvantages. The most significant of these disadvantages are the small yields of dinitrodurene and the large amounts of by-products. These disadvantages are illustrated in Example 1 (comparison example) of the present patent specification.

Admittedly, the nitration of durene in sulfuric acid suspension represents an improvement over the nitration of a solution in an organic solvent. However, the process described in U.S. Pat. No. 3,153,099 has serious disadvantages. For example, the reaction temperature range of 5° to 10° C., which is said to be preferred, results in uneconomically long reaction times. This is also confirmed by Example 2 (comparison example) of the present patent specification.

A further disadvantage of the process disclosed in U.S. Pat. No. 3,153,099 is that the end reaction mixture is stirred into an ice-water mixture. Although this use of ice to dilute concentrated sulfuric acid with water in order to control the heat of mixing that is generated is a conventional and practicable method for laboratory scale operations, it is unsuitable for large-scale production processes. This method requires the availability and handling of large amounts of ice, coupled with the considerable technical effort and expenditure involved in producing and transporting the ice. This method also requires processing the ice in large capacity containers, optionally using comparatively powerful stirrer motors. One of the consequences of this process step is that all of the sulfuric acid used for the reaction becomes diluted and must either be disposed of as a valueless waste acid or be reconcentrated (a complicated and expensive process).

A further disadvantage of the process described in U.S. Pat. No. 3,153,099 is that the crude dinitrodurene filtered off is purified only by washing with water. Consequently, impurities such as sulfuric acid trapped in the dinitrodurene particles are not separated. On the other hand, a minimum quality of the dinitrodurene is necessary, especially if the dinitrodurene is to be used to produce durene diamine by reduction as taught at column 3, lines 47 to 50. This generally means that the dinitrodurene that is prepared must be purified in a further process step, for example, by recrystallization.

Only catalytic hydrogenation is technically feasible as a commercial process for the reduction of dinitrodurene to durene diamine. Although other known processes, such as the conversion of dinitrodurene with ammonium sulfide, with zinc or with tin (II) chloride are suitable for conversions on a laboratory scale, for economic and ecological reasons they are unsuitable for large-scale preparation of durene diamine.

The known processes for catalytic hydrogenation in a protic solvent such as ethanol have the disadvantage as regards the conversion of durene diamine with phosgene that the solvent must be substantially completely removed from the reaction mixture. If the solvent is not substantially removed, undesirable reaction products of the solvent with phosgene will be formed during the phosgenation. This means that the solution of durene diamine must be completely evaporated in a complicated process step and the remaining solid durene diamine then must be re-dissolved in an aprotic solvent.

The process described in British Patent 779,806 for the preparation of durene diisocyanate by reacting durene diamine dihydrochloride with phosgene is also affected by serious disadvantages. For example, preparation of durene diamine dihydrochloride using gaseous hydrogen chloride is costly and time-consuming. Likewise, the reaction of the dihydrochloride with phosgene in suspension is laborious and also results in contamination of the process waste gas with comparatively large amounts of hydrogen chloride.

SUMMARY OF THE INVENTION

It is an object of the present invention to provide a technical process for the preparation of durene diisocyanate.

It is also an object of the present invention to provide a process for the production of durene diisocyanate in higher yields without uneconomically long reaction times.

It is a further object of the present invention to provide a process for the production of durene diisocyanate without generating large quantities of waste and by-products.

It is an additional object of the present invention to provide a process for the production of durene diisocyanate that does not require considerable technical effort and expenditure.

It is a further object of the present invention to provide a process for the production of durene diisocyanate in which the individual reaction steps and process stages are matched to one another.

These and other objects which will be apparent to those skilled in the art are accomplished by (1) reacting durene with nitric acid in the presence of sulfuric acid. (2) diluting the resultant reaction mixture with water to form a suspension; (3) mixing the resultant suspension with an aprotic organic solvent to dissolve the dinitrodurene and to form two liquid phases; (4) separating the liquid phases to recover a solution of dinitrodurene in organic solvent; (5) hydrogenating the dinitrodurene in the presence of a catalyst; (6) removing water and catalyst from the hydrogenated mixture; and (7) phosgenating the diaminodurene from (5).

DETAILED DESCRIPTION OF THE INVENTION

The present invention is an improved process for the preparation of durene diisocyanate by reaction of durene with nitric acid in sulfuric acid, catalytic hydrogenation of the dinitrodurene that is formed, and phosgenation of the resultant durene diamine. In this process, after the reaction of durene with nitric acid in sulfuric acid has been completed, the liquid phase of the reaction mixture, which is composed substantially of sulfuric acid, is diluted by mixing it with water. The resultant suspension is intensively mixed with an aprotic organic solvent that is substantially immiscible with water and is inert with respect to hydrogen to dissolve the dinitrodurene in the solvent and form a mixture composed of two liquid phases. The solution of dinitrodurene in the solvent is separated from this mixture by phase separation and then optionally purified by extraction with water. The dinitrodurene solution thus obtained is subjected to hydrogenation in the presence of a solid, insoluble catalyst, optionally after concentration by distillative separation of solvents. The water and the catalyst are separated from the hydrogenated reaction mixture and the remaining solution of the resultant durene diamine is then phosgenated.

It was extremely surprising that the process of the present invention produces such high yields of durene diisocyanate, even though the intermediate products dinitrodurene and durene diamine are not isolated and separately purified. What is particularly surprising is the fact that dinitrodurene can be separated in such a state of purity from the reaction mixture formed by the reaction of durene with nitric acid merely by dissolution in an aprotic solvent and that the subsequent catalytic hydrogenation can be successfully carried out.

In the process of the present invention, the reaction of durene with nitric acid in sulfuric acid is largely carried out in accordance with the procedure disclosed in U.S. Pat. No. 3,153,099 with the exception that no working-up of the product dinitrodurene is conducted in the process of the present invention.

In the process of the present invention, durene is used in finely divided form in order to achieve as complete a conversion as possible in suspension.

In order to prepare the suspension used in the process of the present invention, durene is mixed with from 5 to 20 times, preferably from 7 to 15 times the amount by weight of concentrated sulfuric acid. The concentrated sulfuric acid generally has a water content of from 2 to 40 wt. %, preferably from 4 to 20 wt. %.

Pure nitric acid can be used for the reaction with durene. Mixtures of nitric acid with sulfuric acid and/or water may, however, also be used. The proportion of sulfuric acid in such mixtures may be from 0 to 75 wt. % and the proportion of water may be from 0 to 40 wt. %.

In the nitration reaction, nitric acid is used in amounts of from about 2.0 to about 2.2 moles, preferably from about 2.0 to about 2.1 moles, for each 1 mole of durene.

The reaction of durene with nitric acid is carried out in the process of the present invention at temperatures of up to 15° C., preferably at from 10° to 15° C., most preferably at from 11° to 13° C. Although reaction temperatures below 10° C. are possible in principle, the resultant low reaction velocity increases the danger that the concentration of nitric acid in the reaction mixture will increase. Increased nitric acid concentration could give rise to an uncontrollable exothermic reaction. To minimize this safety risk, reaction temperatures of less than 10° C. should generally be avoided.

In one embodiment of the present invention, a substantial proportion of the liquid phase is separated from the nitrated reaction mixture by filtration or centrifugation of the dinitrodurene. The proportion of the spent acid separated in this way is generally from about 50 to about 95 wt. %, preferably from about 60 to about 90 wt. % of the overall liquid phase. The amount of spent acid separated is limited by the efficiency of the filtration or centrifugation process.

In a preferred embodiment of the present invention, the spent acid is reused for a subsequent reaction of durene with nitric acid. To this end, the spent acid is generally mixed with additional amounts of concentrated or aqueous or optionally pure sulfuric acid before the nitration reaction. The concentration and amount of added sulfuric acid depend on the amount and composition of the separated spent acid. In general, however, an attempt is made to use approximately the same weight ratios of durene, sulfuric acid and water for each reaction of durene with nitric acid.

In accordance with the process of the present invention, the end reaction mixture of the reaction of durene with nitric acid is mixed with water. If the process is not carried out according to the special embodiment (i.e., by separating the prepared crude dinitrodurene by filtration or centrifugation before mixing with water), it is generally convenient to add water to the reaction vessel and then stir the reaction mixture into the water. It may, however, also be advantageous to mix the end reaction mixture in a continuous stream with a water stream in a mixing unit and thereby cool the mixture.

If the crude dinitrodurene is separated by filtration or centrifugation before mixing with water, it is convenient to suspend the dinitrodurene filter cakes in the water. If desired, the resultant suspension may at the same time also be conveyed to another vessel by the water flow.

The amount of water used for the mixing depends on how much sulfuric acid is mixed with the crude dinitrodurene. Normally, sufficient water is used so that the resultant liquid contains less than 40 wt. %, preferably less than 30 wt. % of sulfuric acid. In general, it is convenient to use sufficient water so that the temperature of the resultant mixture is not more than 100° C. In order to avoid use of an uneconomically large amount of water, it may be advantageous to carry out the mixing with water under efficient external cooling. However, the cooling is generally not necessary if the reaction mixture has been freed (e.g., by filtration or centrifugation) from a substantial proportion of the liquid phase before mixing with water.

In the process of the present invention, the suspension of crude dinitrodurene formed by mixing with water is intensively mixed with an aprotic organic solvent that is substantially immiscible with water. Suitable solvents are those compounds that are inert with respect to aqueous sulfuric acid and durene diisocyanate and are also inert under the conditions of the catalytic hydrogenation and the phosgenation conditions. Examples of suitable solvents include: isooctane, cleaning naphtha, decahydronaphthalene, toluene, m-xylene, 1,2,3,4-tetrahydronaphthalene, chlorobenzene, o-dichlorobenzene, 2-chlorotoluene and 1-chloronaphthalene. Mixtures of suitable solvents may also be used in the process according to the invention. However, toluene or chlorobenzene is preferably used as solvent.

In the present invention, the intensive mixing of the dinitrodurene suspension with the organic solvent may take place at low temperatures. The mixing is, however, conveniently carried out at elevated temperatures in order to accelerate the dissolution process. The temperature is below the boiling point of the relevant solvent and is generally from 30 to 95° C. It may be advantageous to adjust the temperature of the aqueous dinitrodurene suspension to about 90 to 95° C. by choosing a correspondingly small amount of water for the mixing to achieve the desired elevated temperature on dissolution in the solvent. Obviously it is also possible to raise the temperature by using a heated solvent and/or by external heating during dissolution.

The amount of solvent used to dissolve the dinitrodurene depends on the solvent power of the solvent and on the temperature of the mixture and can easily be determined by appropriate preliminary experiments. It is convenient not to use significantly more solvent than is necessary to dissolve the dinitrodurene. A high dilution with solvent is in general disadvantageous because large capacity vessels are then necessary for preparing and processing the solution. Amounts of solvent in the range from 3 to 100 kg, preferably from 4 to 20 kg for each 1 kg of prepared dinitrodurene, are generally used.

The separation of the dinitrodurene solution from the aqueous phase may be carried out in the process of the present invention by phase separation. The amount of time necessary for a sufficient separation depends to a large extent on the composition of the phases and on the nature of the solvent that is used. In order to achieve as rapid a phase separation as possible, the concentrations of the phases are conveniently chosen so that the densities of the phases will be significantly different.

After separation of the organic phase, it may be advantageous to purify that phase by intensive mixing with water and an additional phase separation. This is particularly advantageous if the organic phase still contains a significant proportion of emulsified aqueous acid due to sluggish phase separation.

Extremely dilute solutions may be used for the hydrogenation of the dinitrodurene. In general, however, it is convenient to hydrogenate solutions that are as concentrated as possible in order to achieve high space-time yields. It may therefore be advantageous to separate part of the solvent from the dinitrodurene solutions by distillation before the hydrogenation. Solutions of dinitrodurene with a dinitrodurene concentration of 8 to 40 wt. % are accordingly advantageous.

In the process of the present invention, the dinitrodurene solution is hydrogenated in the presence of a solid catalyst that is practically insoluble in the solvent. Catalysts that are conventionally used in the art for the catalytic hydrogenation of nitroaromatics are suitable for this purpose. Examples of suitable catalysts include: Raney nickel, Raney nickel-iron and Raney cobalt. Precious metal catalysts such as palladium or platinum may of course in principle also be used, but are in general less suitable for economic reasons and the danger of nuclear hydrogenation.

The amount of catalyst used for the hydrogenation depends on the nature of the catalyst, on the type of solvent, and on the concentration and purity of the dissolved dinitrodurene, and varies within a wide range. The optimum weight ratio may easily be determined by suitable preliminary experiments. In general, amounts of catalyst in the range from 0.1 to 10 kg, for each 100 kg of dinitrodurene to be hydrogenated, are used.

The reaction temperature in the catalytic hydrogenation of the dinitrodurene solution also depends on the type of catalyst that is employed and on the type of solvent that is used, and may range from 50 to 250° C.

In the process of the present invention, the catalytic hydrogenation of the dinitrodurene solution may be carried out at a hydrogen pressure of from 1.1 to 200 bar, preferably from 3 to 100 bar.

The end reaction mixture of the catalytic hydrogenation is a multiphase mixture that contains, in addition to the solution of durene diamine in the organic solvent, the catalyst as a solid phase as well as water from the hydrogenation reaction as a second liquid phase. In the present invention, the water and the catalyst may be conveniently completely removed from the reaction mixture before the durene diamine solution is used in the phosgenation.

In a preferred embodiment of the invention, the reaction mixture is freed from water by partial distillation before separating the catalyst. If the hydrogenation is carried out at a temperature above the boiling point of the solvent, it may be advantageous to cool the end reaction mixture by flash evaporation. This releases pressure in the pressurized reactor that is used, cools the mixture, and partially distills the mixture to separate water without additional expenditure of energy. After the pressure compensation, sufficient solvent may be distilled off together with the water until the reaction mixture is practically anhydrous. This can take place directly after the flash evaporation in the pressurized reactor. No additional distillation vessel is required.

The separation of the catalyst from the reaction mixture of the hydrogenation or from the anhydrous durene diamine solution may be carried out by any of the methods conventionally used in the art (e.g., by filtration or centrifugation).

The reaction of the anhydrous and catalyst-free solution of crude durene diamine with phosgene in conventional amounts (ca. 2 to 8 moles, preferably 3 to 6 moles of phosgene for each 1 mole of durene diamine) to form durene diisocyanate may be carried out by conventional cold-hot phosgenation. This means that a solution of phosgene in the organic solvent that was, for example, previously used is first added at a low temperature (from about 0 to 30° C.) to the phosgenation reactor, the durene diamine solution is mixed in, optionally while cooling. The resultant suspension is then heated to reflux and the reaction is completed under reflux, optionally with the addition of more phosgene.

In a preferred embodiment of the process of the present invention, the optionally hot durene diamine solution is intensively continuously mixed with a solution of phosgene in the solvent in a mechanically driven mixing apparatus, and the resultant suspension is passed to a downstream reactor where the reaction is brought to completion. Conventional equipment used in the art, for example pumps or mixers equipped with teeth, are suitable as mixing apparatus. Use of a mixing apparatus producing a uniform mixing due to shear forces minimizes the formation of by-products. Further, the reaction mixture does not have to be cooled, but can be heated directly to reflux in the downstream reactor.

After completion of the phosgenation, the reaction mixture is normally worked up by distillative separation of the phosgene that is still present together with part of the solvent. The durene diisocyanate that is formed can then be recovered by crystallization and purified by recrystallization, as described in British Patent Specification 779,806. The diisocyanate may be conveniently recovered by distillation and purified by fractional distillation. Durene diisocyanate can be distilled without decomposition at temperatures below 200° C. For this purpose, reduced pressures (e.g., those that can be produced without difficulty on a large industrial scale such as pressures of from 1 to 22 mbar) are necessary.

The distillative working-up of the reaction mixture is more advantageous than working-up by means of crystallization because it is substantially less complicated and produces durene diisocyanate of a higher degree of purity. Also, the solvent is recovered in a pure form and can therefore be used again to dissolve the crude dinitrodurene. Finally, fractional distillation makes it possible to recover any small amount of unreacted durene that may still possibly be contained in the crude product in a pure form suitable for re-use in a subsequent nitration.

The process of the present invention may as a whole or in individual partial steps be carried out continuously or batchwise.

Significant advantages of the process of the present invention over the prior art include:

The intermediate products dinitrodurene and durene diamine are not worked up in a complicated manner as solid products, but in an easier to handle dissolved form.

The intermediate products dinitrodurene and durene diamine are not isolated and purified in a complicated manner, but are processed directly after their preparation.

Water is employed for diluting the sulfuric acid and not the more difficult to handle ice used in the prior art.

Use of only one organic solvent for the overall preparation process reduces the amount of equipment and apparatus such as storage vessels and distillation columns necessary to carry out the process.

The process is substantially less environmentally harmful due to the separation and re-use of spent acid in the reaction of durene with nitric acid.

The durene diisocyanate prepared in accordance with the present invention represents a valuable starting product for the preparation of polyurethane plastics.

The invention is further illustrated but is not intended to be limited by the following examples in which all parts and percentages are by weight, unless otherwise specified.

EXAMPLES

The following examples are intended to illustrate the process according to the invention in more detail:

Example 1

Comparison Example

A solution of 100 g of durene in 600 ml of n-hexane was placed in a 2 liter capacity round-bottom flask that was provided with a dropping funnel. 100 g of nitric acid (100%) were added dropwise to the solution within one hour while stirring at 20 to 25° C. The heat of reaction was dissipated by cooling in an ice bath. The reaction mixture was then stirred for a further two hours at 25° C. and extracted by shaking with 500 ml of water in a separating funnel. After separating the aqueous phase, the organic phase was freed from n-hexane by distillation. A clear yellow liquid remained behind. According to gas chromatography and infra-red spectroscopy analysis, the reaction product contained, in addition to a small amount of durene, several unidentifiable compounds. Dinitrodurene could not be detected in the reaction product mixture.

Example 2

Comparison example 110 kg of 95.8 percent sulfuric acid were placed in an enamel boiler that was equipped with an enamel stirrer and an external brine cooling solution and cooled to 5° C. 10.0 kg of ground durene were added to the boiler while stirring. The mixture was stirred for 15 minutes and a homogeneous suspension was formed. 2.1 kg (corresponding to 6.4% of the stoichiometrically necessary amount) of an acid mixture (28.4 wt. % nitric acid; 57.6 wt. % sulfuric acid; 14.0 wt. % water) were stirred into the suspension within 15 minutes while gently cooling at 5 to 7° C. Only a small heat of reaction was observed, and the addition of the acid mixture was therefore discontinued. A sample was taken from the reaction mixture, stirred into ice and then analyzed. It was found that the nitric acid conversion was only 36%.

Example 3

Preparation of Durene Diisocyanate 136 kg of concentrated sulfuric acid (89.8 wt. % sulfuric acid and 10.2 wt. % water) were added to an enamel boiler that was equipped with an enamel stirrer and an external brine cooling solution and cooled to 10° C. 11.4 kg of ground durene were added to the boiler while stirring. The mixture was stirred for 15 minutes and a homogeneous suspension formed. 32.5 kg of nitrating acid (33 wt. % nitric acid; 67 wt. % sulfuric acid) were metered into this suspension within 2.8 hrs under good brine with cooling and vigorous stirring, so that the reaction temperature was 11 to 13° C. The pulp-like mixture was then stirred for an additional hour at 11 to 13° C. 400 l of water at 15° C. were added to a further boiler equipped with a stirrer and external cooling. The reaction mixture was then metered into the water, while stirring and cooling, so that the resultant temperature did not exceed 95° C. 100 l of chlorobenzene were added to the resultant readily stirrable suspension and the whole mixture was stirred intensively for 30 minutes. After phase separation (30 minutes), the lower, aqueous phase was separated. 40 l of chlorobenzene were distilled off from the remaining organic phase. 400 g of Raney nickel were added to the thus-concentrated solution, and hydrogenation was carried out in an autoclave at 180° C. and at a pressure of 40 to 50 bar. The uptake of hydrogen was complete after 4.5 hrs. The autoclave was then cooled to 130° C. by flash evaporation. Chlorobenzene and water were then distilled off from the reaction mixture until the mixture was free of water (22 l of chlorobenzene in total). The reaction mixture was then freed from Raney nickel under the addition of hot anhydrous chlorobenzene (14 l in total) by filtration through a pressure suction filter at 110 to 120° C. 110 kg of a cold 25 wt. % solution of phosgene in chlorobenzene were then added to the clear filtrate, which was at a temperature of 110° C. The resultant reaction mixture was added to a boiler, heated to reflux under the gentle introduction of phosgene and phosgenated for a further hour under reflux. A clear solution formed. The reaction mixture was freed from excess phosgene and chlorobenzene by distillation. The remaining crude product was flash distilled under a reduced pressure of 18 mbar. 13.5 kg of yellowish distillate were obtained. According to gas chromatographic analysis, this distillate contained 97.0% of durene diisocyanate and 2.7% of durene. The product was purified by fractional vacuum distillation and yielded a colorless distillate having a boiling point of 182–184° C. at 18 mbar, which solidified to form crystals having a melting point of 113–114° C.

Example 4

Preparation of Durene Diisocyanate 11.4 kg of durene in 136 kg of concentrated sulfuric acid were reacted with 32.5 kg of nitrating acid in the same manner as in Example 3. After the addition of the nitrating acid, the reaction mixture was stirred for an additional hour at 11 to 13° C. and then filtered through a pressure suction filter by means of nitrogen pressure. 125 kg of spent acid (88.3 wt. % sulfuric acid; 10.3 wt. % water) were thereby obtained as a clear dark liquid. The filter cake was suspended with 120 l of water at 15° C. and rinsed into a boiler. 100 l of chlorobenzene were added to the easily stirrable 70° C. suspension that was obtained and the whole mixture was stirred intensively for 30 minutes. The further process steps were carried out as in Example 3. 13.7 kg of flash distilled durene diisocyanate containing 96.8 wt. % of diisocyanate were obtained.

Example 5

Preparation of Durene Diisocyanate

Durene diisocyanate was prepared in the same way as in Example 4, with the exception that the spent acid from Example 4 (125 kg; 88.3% sulfuric acid) obtained in the filtration of crude dinitrodurene, to which an additional 13 kg of concentrated sulfuric acid (7.0 wt. % water) were added before the reaction, was used for the nitration of durene (11.4 kg). After completion of the nitration, 128 kg of spent acid (87.3 wt. % sulfuric acid; 10.2 wt. % water) were obtained in the filtration of dinitrodurene.

Flash distillation of the crude durene diisocyanate yielded 13.5 kg of yellowish product containing 2.6% of durene and 96.5% of durene diisocyanate.

Example 6

Preparation of Durene Diisocyanate 11.4 kg of durene in 136 kg of concentrated sulfuric acid were reacted with 32.5 kg of nitrating acid in the same manner as described in Example 3. The end reaction mixture was stirred into 400 l of water. The suspension obtained was intensively mixed with 120 l of toluene at 70° C. for 45 minutes. The lower, aqueous phase was separated after the subsequent phase separation. 60 l of toluene were distilled off from the remaining organic phase. 400 g of Raney nickel were added to the solution concentrated in this way and hydrogenation was carried out in an autoclave at 170° C. and at a pressure of 41 to 54 bar. The uptake of hydrogen was complete after 4 hours. The autoclave was cooled to 110° C. by flash evaporation. Toluene and water were then distilled off from the reaction mixture until the mixture was free from water. The reaction mixture was then freed from Raney nickel by filtering through a pressure suction filter at 100 to 110° C. 110 kg of a cold 25 wt. % solution of phosgene in toluene were then added via a toothed mixer to the clear 100° C. filtrate. The resultant reaction mixture was added to a boiler, heated to reflux under gentle introduction of phosgene, and phosgenated for an additional 2 hours under reflux. A clear solution formed. The reaction mixture was freed from excess phosgene and toluene by distillation. The remaining crude product was flash distilled under a reduced pressure of 18 mbar. 13.6 kg of 96.9% pure durene diisocyanate were thereby obtained.

As Examples 3 to 6 show, high yields of durene diisocyanate can be obtained in a technically simple manner in the three-stage reaction process of the present invention.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of 2,3,5,6-tetramethyl-1,4-diisocyanatobenzene comprising:

a) reacting 1,2,4,5-tetramethylbenzene with nitric acid in the presence of sulfuric acid to form 2,3,5,6-tetramethyl-1,4-dinitrobenzene, b) diluting liquid reaction mixture from a) with water to form a suspension, c) intensively mixing the suspension from b) with an aprotic organic solvent that is substantially immiscible with water and inert with respect to hydrogen to dissolve 2,3,5,6-tetramethyl dinitrobenzene present in the suspension and to form two liquid phases, d) separating the liquid phases from c) to recover a solution of 2,3,5,6-tetramethyl dinitrobenzene in organic solvent, e) hydrogenating the 2,3,5,6-tetramethyl-1,4-dinitrobenzene in the presence of a Raney catalyst, a palladium catalyst or a platinum catalyst to form 2,3,5,6-tetramethyl-1,4-diaminobenzene, f) removing water and the Raney catalyst, palladium catalyst or platinum catalyst from the hydrogenated mixture to obtain a solution of 2,3,5,6-tetramethyl-1,4-diaminobenzene, and g) phosgenating the 2,3,5,6-tetramethyl-1,4-diaminobenzene solution from f) to form 2,3,5,6-tetramethyl-1,4-diisocyanatobenzene.

2. The process of claim 1 in which the solution of 2,3,5,6-tetramethyl dinitrobenzene solution from step d) is concentrated by distillation to remove solvent before step e) is carried out.

3. The process of claim 1 in which the solution of 2,3,5,6-tetramethyl-1,4-dinitrobenzene from step d) is purified by extraction with water prior to step e).

4. The process of claim 1 in which the reaction of step a) is carried out at a temperature of from about 10 to about 15° C.

5. The process of claim 1 in which spent acid is removed from the reaction mixture generated in step a) by filtration or centrifugation prior to step b).

6. The process of claim 5 in which the removed spent acid is used in a subsequent step a).

7. The process of claim 1 in which the aprotic organic solvent is toluene.

8. The process of claim 1 in which the aprotic organic solvent is chlorobenzene.

9. The process of claim 1 in which step f) is carried out by:

(1) distilling the hydrogenated mixture to completely remove any water present, (2) separating the Raney catalyst, palladium catalyst or platinum catalyst from the mixture of (1), and (3) diluting the mixture from (2) with the same solvent that was used in c).

10. The process of claim 9 in which step g) is carried out by (1) continuously and intensively mixing the mixture from f) (3) with a solution of phosgene in an organic solvent in a mechanically operated mixing device, (2) adding the mixture from g) (1) to a downstream reactor, and (3) increasing the temperature in the downstream reactor to promote completion of the 2,3,5,6-tetramethyl-1,4-diisocyanatobenzene-forming reaction.

11. The process of claim 10 in which phosgene is added to the downstream reactor in step g) (3).

12. The process of claim 1 in which step g) is carried out by (1) continuously and intensively mixing the mixture from f) with a solution of phosgene in an organic solvent in a mechanically operated mixing device, (2) adding the mixture from g) (1) to a downstream reactor, and (3) increasing the temperature in the downstream reactor to promote completion of the 2,3,5,6-tetramethyl-1,4-diisocyanatobenzene-forming reaction.

13. The process of claim 12 in which phosgene is added to the downstream reactor in g) (3).

\* \* \* \* \*